(12) United States Patent
Dosmann

(10) Patent No.: US 6,473,190 B1
(45) Date of Patent: Oct. 29, 2002

(54) OPTICAL VOLUME SENSOR

(75) Inventor: Andrew J. Dosmann, Granger, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/523,716

(22) Filed: Mar. 13, 2000

(51) Int. Cl.⁷ .............................................. G01B 11/28
(52) U.S. Cl. ....................... 356/627; 356/628; 356/630; 250/559.29; 250/559.31
(58) Field of Search ................................ 358/625, 627, 358/628, 629, 630, 634, 635, 636, 640, 614, 615; 250/559.29, 559.31, 215

(56) References Cited

U.S. PATENT DOCUMENTS

| | | | | |
|---|---|---|---|---|
| 4,693,607 A | * | 9/1987 | Conway | 356/627 |
| 4,767,212 A | * | 8/1988 | Kitahashi et al. | 356/627 |
| 5,184,733 A | * | 2/1993 | Arnarson et al. | 356/627 |
| 5,555,090 A | * | 9/1996 | Schmutz | 356/630 |
| 5,699,161 A | * | 12/1997 | Woodworth | 356/627 |
| 6,061,645 A | * | 5/2000 | Bengala et al. | 356/630 |
| 6,069,696 A | * | 5/2000 | McQueen et al. | 356/326 |
| 6,202,493 B1 | * | 3/2001 | Cantral et al. | 73/800 |

* cited by examiner

Primary Examiner—Richard A. Rosenberger
Assistant Examiner—Sang H. Nguyen
(74) Attorney, Agent, or Firm—Jerome L. Jeffers

(57) ABSTRACT

An optical sensor for measuring the volume of an object, the object having a top and a side. The optical sensor comprises a source of light and a light sensor adapted to measure the amount of light reflected off the side and off the top of the object, wherein the measured amount of the light reflected off the side and the top of the object correlates to a height and a diameter of the object. At least one optical device is adapted to direct light reflected off the side of the object to the light sensor, and at least one optical device is adapted to direct light reflected off the top of the object to the light sensor.

61 Claims, 8 Drawing Sheets

OPTICAL VOLUME SENSOR

FIELD OF THE INVENTION

The present invention relates generally to volume measurement devices, and, more particularly, to an optical volume sensor for measuring the volume of a drop of blood.

BACKGROUND OF THE INVENTION

It is often necessary to quickly and inexpensively measure the volume of an object. One example of a need for volume measurement is in connection with a blood glucose monitoring system where it may be necessary to measure the volume of a drop of blood.

Those who have irregular blood glucose concentration levels are medically required to regularly self-monitor their blood glucose concentration level. An irregular blood glucose level can be brought on by a variety of reasons including illness such as diabetes. The purpose of monitoring the blood glucose concentration level is to determine the blood glucose concentration level and then to take corrective action, based upon whether the level is too high or too low, to bring the level back within a normal range. The failure to take corrective action can have serious implications. When blood glucose levels drop too low—a condition known as hypoglycemia—a person can become nervous. shaky, and confused. That person's judgment may become impaired and that person may eventually pass out. A person can also become very ill if their blood glucose level becomes too high—a condition known as hyperglycemia. Both conditions, hypoglycemia and hyperglycemia, are both potentially life-threatening emergencies.

One method of monitoring a person's blood glucose level is with a portable, hand-held blood glucose testing device. A prior art blood glucose testing device 100 is illustrated in FIG. 1. The portable nature of these devices 100 enables the users to conveniently test their blood glucose levels wherever the user may be. The glucose testing device contains a test sensor 102 to harvest the blood for analysis. The device 100 contains a switch 104 to activate the device 100 and a display 106 to display the blood glucose analysis results. In order to check the blood glucose level, a drop of blood is obtained from the fingertip using a lancing device. A prior art lancing device 120 is illustrated in FIG. 2. The lancing device 120 contains a needle lance 122 to puncture the skin. Some lancing devices implement a vacuum to facilitate the drawing of blood. Once the requisite amount of blood is produced on the fingertip, the blood is harvested using the test sensor 102. The test sensor 102, which is inserted into a testing unit 100, is brought into contact with the blood drop. The test sensor 102 draws the blood to the inside of the test unit 100 which then determines the concentration of glucose in the blood. Once the results of the test are displayed on the display 106 of the test unit 100, the test sensor 102 is discarded. Each new test requires a new test sensor 102.

One problem associated with some lancing devices is that the requisite amount of blood for accurate test results is not always obtained. Roughly thirty percent of lances to do not produce enough blood for accurate analysis. The amount of blood obtained from each lance varies between zero and ten microliters ("$\mu l$"). For an accurate result, at least two $\mu l$ of blood must be obtained. If less than this amount is produced, the test results may be erroneous and a test sensor is wasted. More serious an issue, however, is that the user may be relying on inaccurate results. Obviously, because of the serious nature of the medical issues involved, erroneous results are not preferred.

Another problem associated with conventional lancing devices is that there is no mechanism to let the user know whether the correct amount of blood has been obtained for accurate analysis. Typically, the test units come with instructions containing a graphical illustration of the actual size of the blood drop required for accurate testing. However, this visual comparison is subjective and often produces inconsistent results. To insure the requisite amount of blood is produced, users often overcompensate by squeezing or otherwise manipulating their fingers to produce larger than necessary drops of blood. However, this adds more time to the overall testing process and also results in an increased amount of wasted blood.

The inconsistent results produced by conventional lances has impeded the integration of the lancing device, the harvesting device, and the blood glucose analysis device into a single unit. Because the analysis may begin even though the requisite amount of blood has not been obtained, it appears problematic to combine the lancing with the actual harvesting due to the potentially inaccurate results.

SUMMARY OF THE INVENTION

According to one embodiment of the present invention, there is an optical sensor for determining the volume of an object. One application of the optical sensor is for use in a blood glucose monitoring system which integrates the lancing device. the harvesting device, and the blood glucose analysis device into a single unit. In accordance with the present invention, the optical sensor comprises a source of light and a light sensor adapted to measure an amount of light reflected off the side and off the top of a drop of blood, wherein the measured amount of the light reflected off the side and the top correlates to a height and a diameter of the blood drop. At least one optical device is adapted to direct light reflected off the side of the object to the light detector, and at least one optical device is adapted to direct light reflected off the top of the object to the light detector.

The above summary of the present invention is not intended to represent each embodiment, or every aspect, of the present invention. Additional features and benefits of the present invention will become apparent from the detailed description, figures, and claims set forth below.

BRIEF DESCRIPTION OF THE DRAWINGS

Other objects and advantages of the invention will become apparent upon reading the following detailed description in conjunction with the drawings in which.

DETAILED DESCRIPTION OF THE PREFERRED EMBODIMENTS

Figure 1:
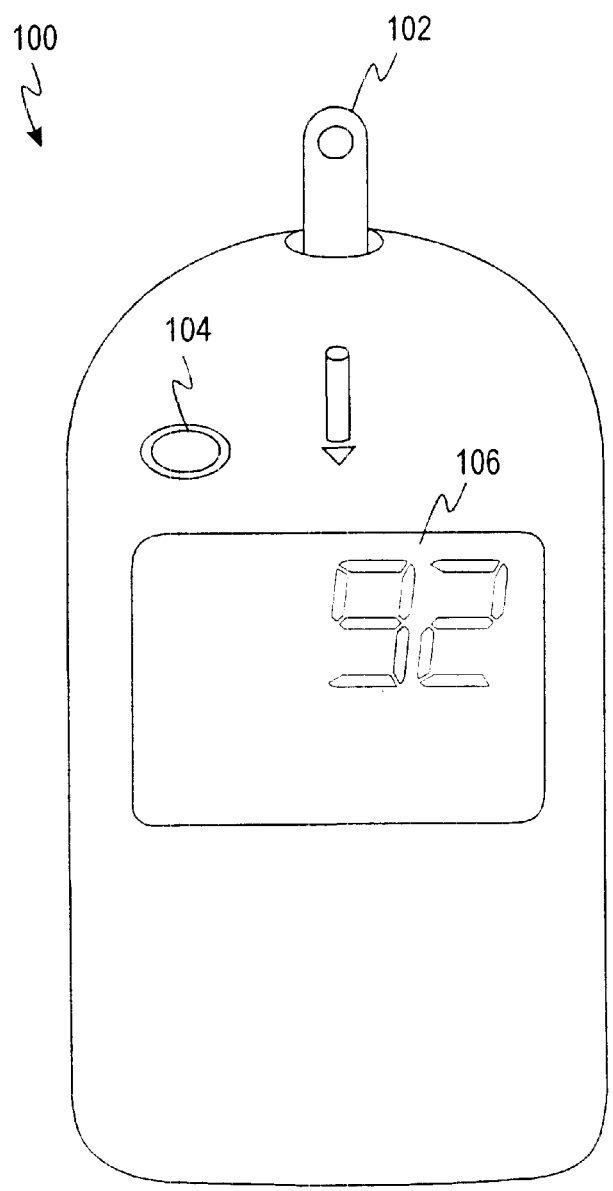
FIG. 1 is a top view of a prior art blood glucose testing device.
Figure 2:
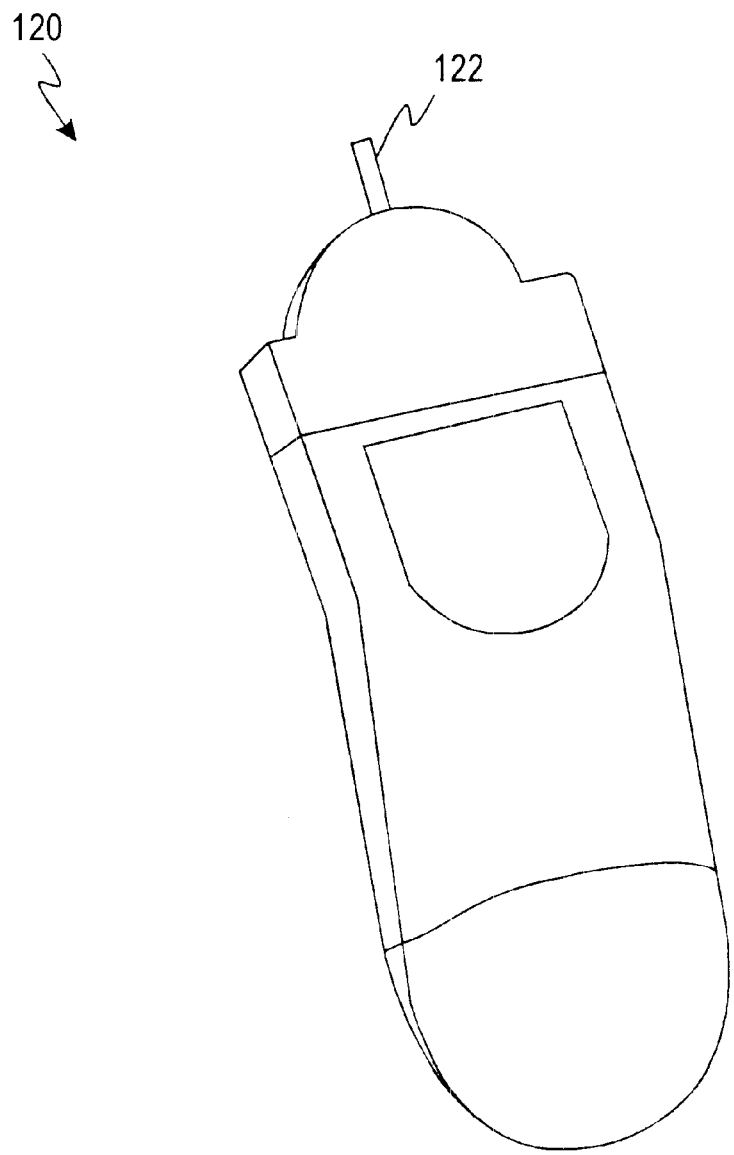
FIG. 2 is a top view of a prior art lance.
Figure 3:
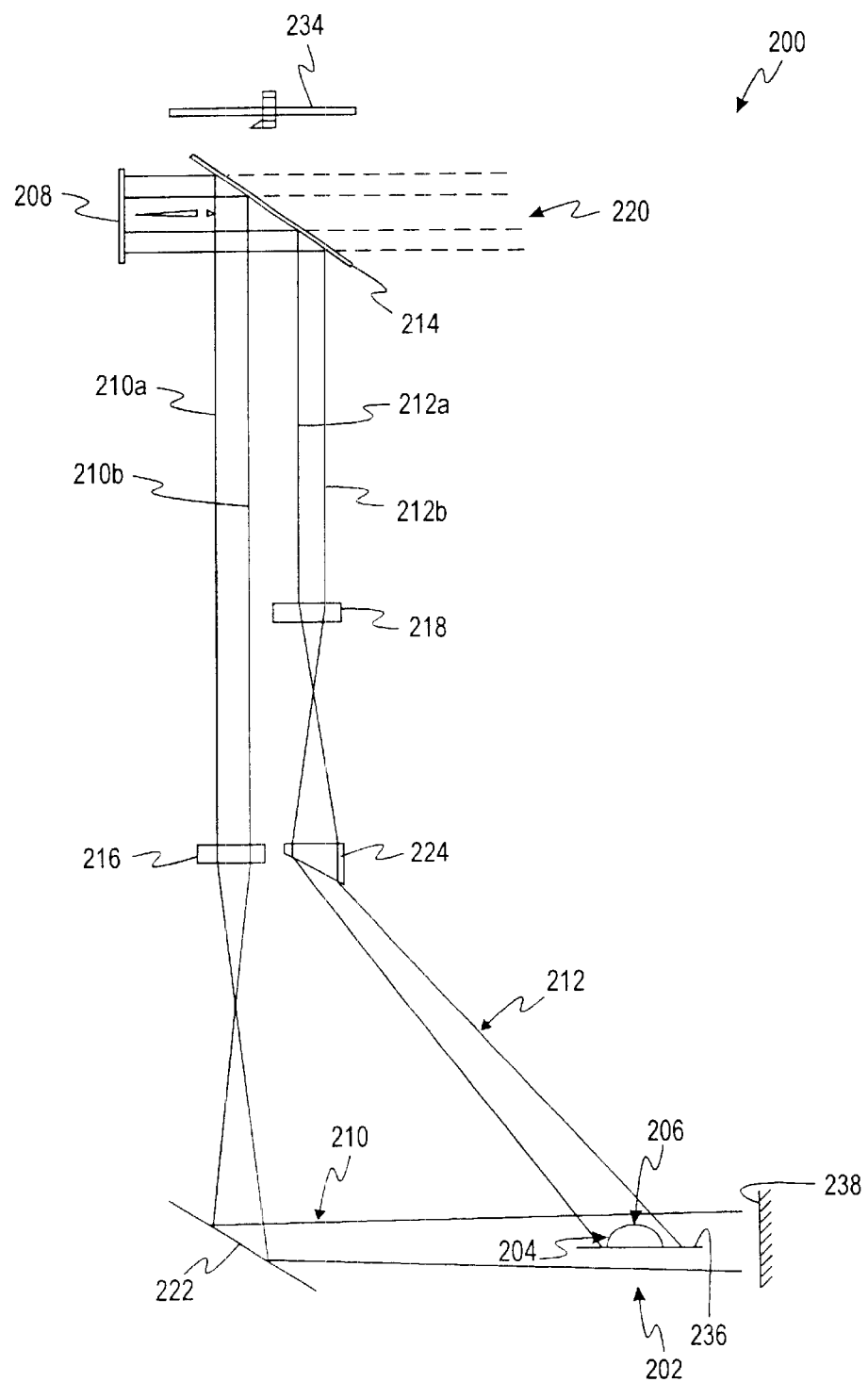
FIG. 3 is an optical design for a optical volume sensor wherein light ray traces are shown illuminating a blood drop according to one embodiment of the present invention.

Referring now to FIG. 3, a design for an embodiment of an optical volume sensor 200 is shown. The volume of a drop of blood 202 is determined by illuminating the blood drop 202 and measuring the amount of light reflected off one side 204 of the blood drop and off a top 206 of the blood drop 202. The blood drop 202 is illuminated by reflecting light from a light source 208 through a series of imaging optics, along light paths 210, 212 onto the side 204 and the top 206 of the blood drop 202. The light directed along the light path 210 illuminates the side 204 of the blood drop 202. The light directed along the light path 212 illuminates the top 206 of the blood drop 202. The side illumination light path 210 has edges 210a, 210b and the top illumination light path 212 has edges 212a, 212b.

The source of light 208 has a wavelength of about 800 nanometers ("nm"). A source of light having a wavelength greater than 750 nm is desirable to avoid significant variation in blood and skin reflectance seen at visible wavelengths from 450 to 750 nm. Utilizing a source of light 208 having a wavelength greater than 750 nm results in a more consistent amount of light reflected off the blood drop 202. The light source 208 is an incandescent light source but can also be one or more light emitting diodes ("LEDs").

Light emitted from the light source 208 is reflected off a beam splitter 214 down through a side view lens 216 and a top view lens 218. In one embodiment of the present invention, the beam splitter 214 is a fifty percent beam splitter 214 causing approximately half of the incoming light to be transmitted through the beam splitter 214 and the remaining approximately half of the incoming light to be reflected by the beam splitter towards the side view lens 216 and the top view lens 218. Thus, in FIG. 3, half of the light incoming from the source of light 208 passes through the beam splitter 214 and the other half of the light is reflected downward along the side illumination light path 210 and the top illumination light path 212. The light transmitted though the beam splitter 214 is labeled with reference number 220.

The light reflected by the beam splitter 214 that is directed along the side illumination light path 210 passes through the side view lens 216 to a mirror 222 which directs the light onto the side 204 of the blood drop 202. The side view lens 216 expands the light so that the light when directed off the mirror 222 over-illuminates the blood drop 204 causing some of the light to be cast upon a white surface 238 disposed adjacent to the blood drop 202.

The light reflected by the beam splitter 214 that is directed along the top illumination light path 212 passes through the top view lens 218 and a wedge lens 224 onto the blood drop 202. The wedge lens 224 directs the light onto the top 206 of the blood drop 202. Similar to the side view lens 216, the top view lens 218 expands the light so that the light when directed though the wedge lens 224 over-illuminates the blood drop 202 causing some of the light to be cast upon an area of skin 236 upon which the blood drop has formed.

When the light comes into contact with the blood drop 202 a portion of that light is absorbed by the blood drop 202 while a portion of the light is reflected off the blood drop 202. Accordingly, the light reflected off the blood drop 202 is less intense than the light illuminating the blood drop 202. The light not coming into contact with the blood drop 202 due to over-illumination is reflected off the skin 236 and off the white surface 238. The white surface 238 has reflectance properties similar to the skin 238. Both the skin 236 and the white surface 238 are more reflective than the blood drop 202. Due to the absorption by the blood drop 202, the light reflected off the blood drop 202 is less intense than the light reflected off the skin 236 and the white surface 238. The blood drop 202 absorbs approximately fifteen percent more light than the skin 236 and the white surface 238. Therefore, the light reflected off the blood drop 202 is approximately fifteen percent less intense than the light reflected off the skin 236 and the white surface 238. It is this amount of the less-intense light reflected off the blood drop 202 which is indicative of the height and the diameter of the blood drop 202.

Figure 4:
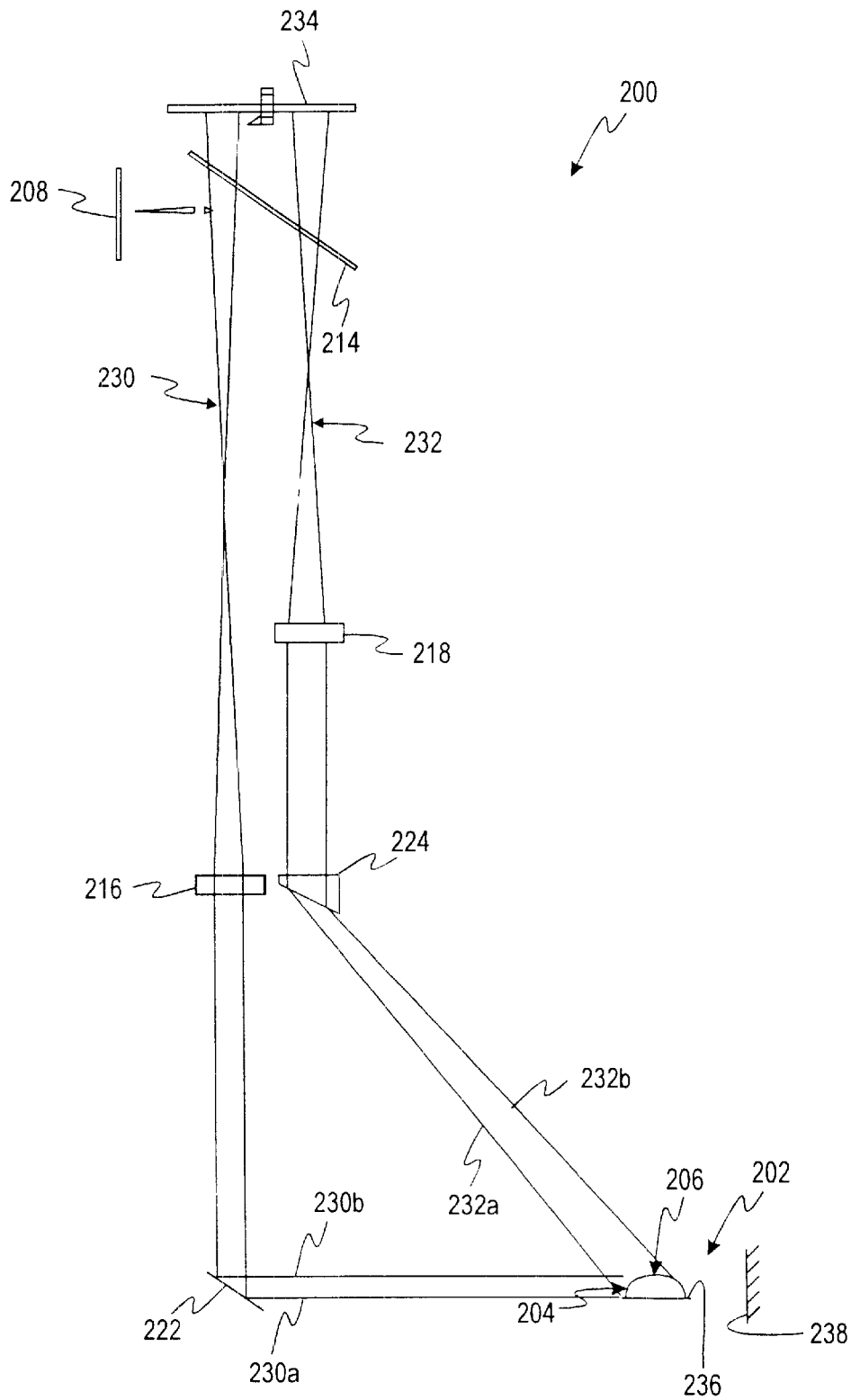
FIG. 4 is an optical design for an optical volume sensor wherein light ray traces are shown reflected off a blood drop according to one embodiment of the present invention.

Referring now to FIG. 4, the light paths 230, 232 of the light reflected off the side 204 and off the top 206 of the blood drop 202, respectively, are illustrated. The side reflected light path 230 has edges 230a, 230b and the top reflected light path 232 has edges 232a, 232b. The light reflected off the side 204 and off the top 206 of the blood drop 202 is directed along the side reflected light path 230 and the top reflected light path 232, respectively, to a light sensor 234. The side reflected light path 230 has edges 230a, 230b and the top reflected light path has edges 232a, 232b.

The light reflected off the side 204 of the blood drop 202 and off the white surface 238 is directed by the mirror 222 back through the side view lens 216. The side view lens 216 brings the side reflected light into focus and images the side reflected light onto the light sensor 234. The side view lens 216 also prevents any scattering of the light directed along the side reflected light path 230. In an alternative embodiment of the present invention, the side view lens 216 can be excluded.

The light reflected off the top 206 of the blood drop 202 and off the skin 236 is directed by the wedge lens 224 through the top view lens 218 onto the light sensor 234. The function of the top view lens 218 is similar to the side view lens 216 in that it brings the top reflected light into focus and images the top reflected light onto the light sensor 234. The top view lens 218 also prevents any scattering of the top reflected light. In an alternative embodiment of the present invention, the side view lens 218 can be excluded.

The light directed along the side and top reflected light paths 230, 232 is transmitted through the beam splitter 214 to the light sensor 234. The beam splitter 214 transmits a portion of the reflected light to the light sensor 234, while reflecting a portion of the light. In the embodiment wherein the beam splitter 214 is a fifty percent beam splitter, about half of the reflected light is transmitted to the light sensor 234.

The light sensor 234 measures the intensity of the reflected light and communicates this information to a processor (not shown). The light reflected off the blood drop 202, the skin 236, and the white surface 238 as well as any external light will be detected by the light sensor 234. The intensities of the light reflected off the blood drop 202, the skin 236, and the white surface 238 are a function of the intensity of the light source 208 and the absorptivity of the blood 202, the skin 236, and the white surface 238. Preferably, there is significant contrast between the light reflected off the blood drop 202 and the light reflected off the skin 236 and/or the white surface 238 due to the skin 236 and the white surface 238 being more reflective than the blood drop 202. Specifically. in the embodiment of the optical volume sensor 200 wherein the light source 234 is an approximately 800 nm light source, the light reflected off the blood drop 202 is approximately fifteen percent less intense than the light reflected off the skin 236 and the white surface 238. Any external light detected by the sensor 234 is expected to have an intensity much less than the light reflected off the blood drop 202, the skin 236, and the white surface 238. The light falling within the expected range of light reflected off the blood drop 202 will be indicative of the height and diameter of the blood drop 202.

In the present invention, the light sensor 234 is a 1×128 pixel line array light detector. Each pixel of the line array light detector individually measures the intensity of light. In operation, the two light paths 230, 232 are directed onto the line array light detector 234. Both light paths 230, 232 will contain light reflected off the blood drop 202 along with light reflected off the skin 236 or the white surface 238 on either side. Accordingly, the less intense light (reflected off the blood drop 202) is surrounded by the more intense light (reflected off the skin 236 and the white surface 238). The width of the less intense light that is reflected off the side 204 and off the top 206 of the blood drop 202 is indicative of the height and diameter of the blood drop 202, respectively. Each pixel correlates to a fixed distance. Accordingly, the more pixels which detect light having an intensity of light reflected off the blood drop 202, the larger the blood drop 202 is. In the embodiment of the optical volume sensor 200 illustrated in FIGS. 3 and 4, the spatial resolution for one pixel viewing the blood drop is 25 micrometers ("$\mu$m") for the height and 50 $\mu$m for the diameter. For example, if thirty pixels detect light reflected off the side 204 of the blood drop 202, the blood drop 202 has a height of approximately 750 $\mu$m or 0.75 millimeters ("mm"), and if 60 pixels detect light reflected off the top 206 of the blood drop 202, the blood drop 202 has a diameter of 3000 $\mu$m or 3 mm.

The design for the optical volume sensor shown in FIGS. 3 and 4 was modeled with LightTools software, manufactured by Optical Research Associates located in Pasadena, Calif. The blood drop 202 was modeled as a spherical lambertian. The light source 208 was modeled as a 800 nm light source.

Figure 5:
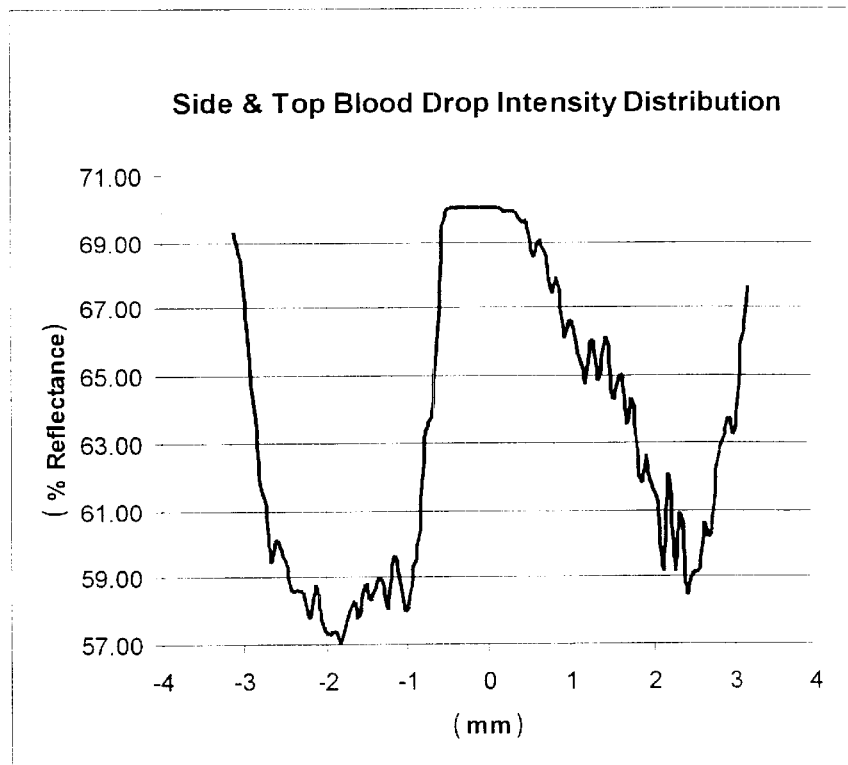
FIG. 5 is a plot of the intensity distribution of the light reflected off the side and off the top of a blood drop according to one embodiment of the present invention.

FIG. 5 shows the intensity distribution of a two $\mu$l blood drop on the line array detector. The side view (blood drop height) is shown on the left-hand side of the plot and the top view (blood drop diameter) is shown on the right-hand side of the plot. The drop in intensity on both the left and right side of the plot correlates to the less intense light reflected off the side 204 and off the top 206 of the blood drop 202. The magnitude of each drop in intensity represents the difference in intensities between the light reflected off the blood drop 202 and the light reflected off the skin 236 or the white surface 238.

Once the height and diameter of the blood drop are determined, the approximate volume of the blood drop 202 is calculated using the following algorithm:

$$\text{Volume} = \frac{1}{2}(\text{Height}) \times (\text{Diameter})^2$$

Under the above example where the height is 0.75 mm and the diameter is 3 mm the volume of the blood drop is approximately 3.4 $\mu$l.

Figure 6:
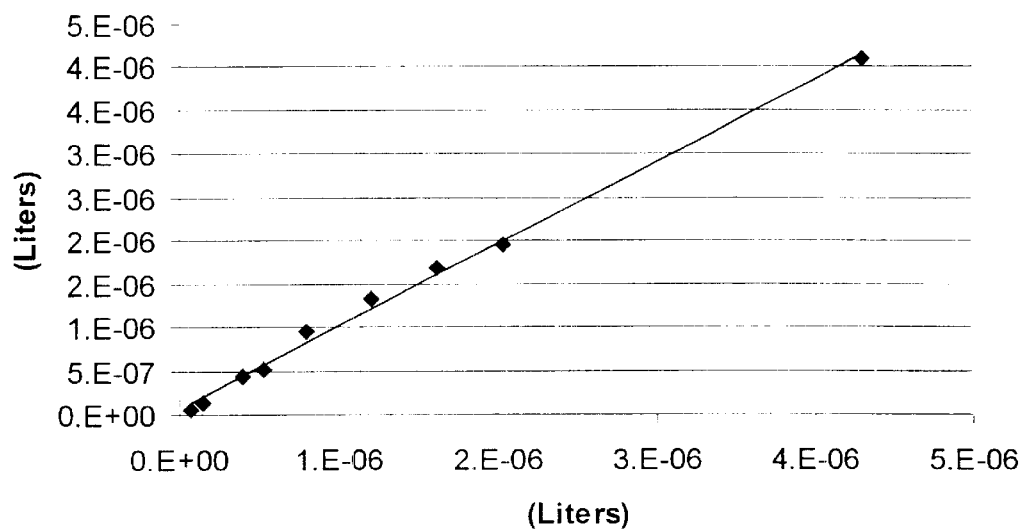
FIG. 6 is a plot of the modeled volume measurements of an optical volume sensor versus the actual modeled volumes according to one embodiment of the present invention.

Using the above algorithm, the optical volume sensor was also modeled with LightTools software for a number of blood drops having volumes ranging from 0.5 to 4.5 $\mu$l. FIG. 6 is a plot of the volumes calculated using the above algorithm versus the actual modeled blood drop volumes. FIG. 6 shows that the modeled optical volume sensor was able to determine the blood volume with good correlation to the actual modeled volume.

Figure 7:
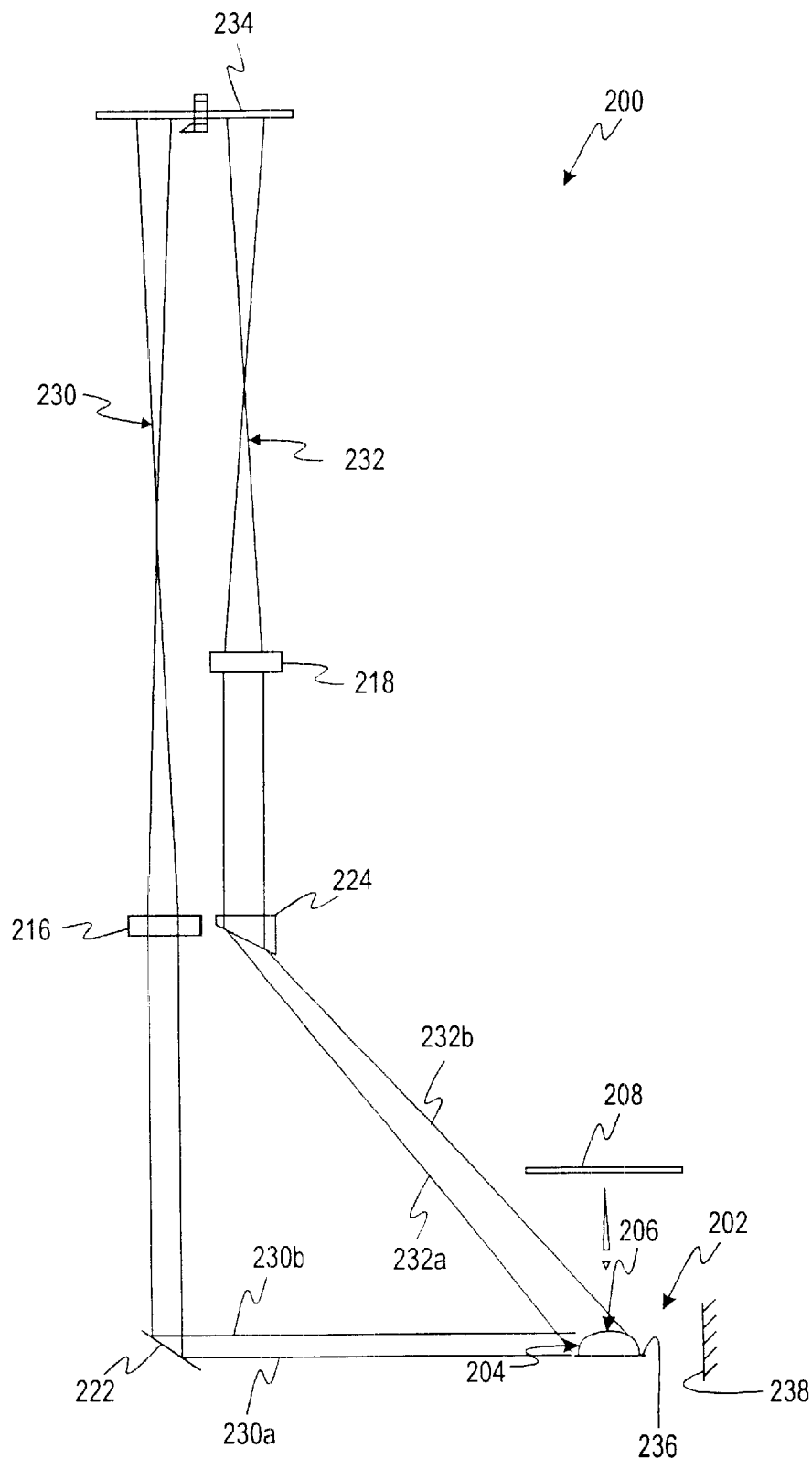
FIG. 7 is an optical design for an optical volume sensor wherein light ray traces are shown reflected off a blood drop according to an alternative embodiment of the present invention.

An alternative embodiment of the optical volume sensor 200 is illustrated in FIG. 7. In the embodiment illustrated in FIG. 7, the light source 208 is disposed above the blood drop 202. Disposing the light source 208 obviates the need for the beam splitter 208 (FIGS. 3 and 4) because it is not necessary to reflect the illuminating light (FIG. 3) or to transmit the reflected light (FIG. 4).

Figure 8:
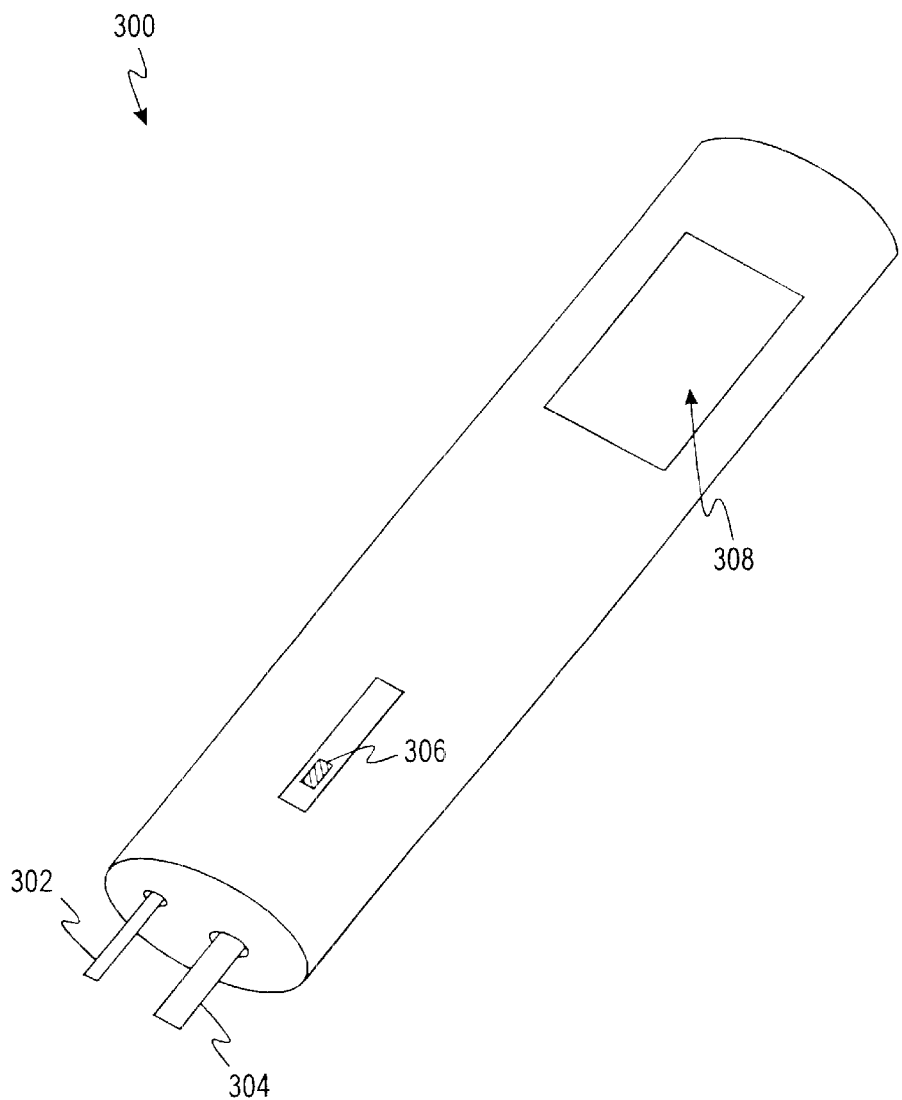
FIG. 8 is a perspective view of an integrated glucose monitoring device according to one embodiment of the present invention.

Referring now to FIG. 8, one application of the present invention is in an integrated blood glucose monitoring system 300 which integrates a lance 302, a test sensor 304 for blood harvesting, and a blood glucose analyzer into a single instrument. The lance 302 comprises a needle which is used to puncture a user's skin in order to obtain a drop of blood. The test sensor 304 is used to harvest the blood drop from the user's fingertip for analysis. The blood glucose monitoring system 300 is activated with a switch 306. After the user's skin is lanced using the lancing component 302 of the system 300, the volume of the blood on the user's skin is measured with an optical volume sensor 300 (FIGS. 3 and 4) to insure the requisite amount of blood is obtained before analysis begins. Once a sufficient amount of blood has been obtained, the test sensor 304 harvests the blood so that the blood glucose level may be analyzed. The results of the analysis are communicated to the user via a display 308.

While the invention is susceptible to various modifications and alternative forms, specific embodiments thereof have been shown by way of example in the drawings and will be described in detail herein. It should be understood, however, that it is not intended to limit the invention to the particular forms disclosed, but, to the contrary, the intention is to cover all modifications, equivalents and alternatives falling within the spirit and scope of the invention as defined by the appended claims.

What is claimed is:

1. An optical sensor for measuring the volume of an object comprising:
   a source of light adapted to illuminate a side and a top of the object;
   a light sensor adapted to measure an amount of light reflected off the side and off the top of the object;
   means for directing light reflected off the side and the top of the object to the light sensor, wherein the amount of light reflected off the side and the top of the object correlates to a height and a transverse dimension of the object; and
   a processor communicatively coupled to the light sensor, the processor determining the volume of the object from a single height measurement of the object and a single transverse dimension measurement of the object.

2. The optical sensor of claim 1 wherein the light has a wavelength greater than about 750 nanometers.

3. The optical sensor of claim 2 wherein the wavelength is about 800 nanometers.

4. The optical sensor of claim 1 wherein the source of light source comprises an incandescent light.

5. The optical sensor of claim 1 wherein the source of light source comprises a plurality of light emitting diodes.

6. The optical sensor of claim 1 wherein the means for directing comprises a mirror being adapted to direct light reflected off the side of the object to the light sensor.

7. The optical sensor of claim 6 wherein the means for directing further comprises a first lens disposed between the mirror and the light detector, the first lens being adapted to image the reflected light directed from the mirror onto the light sensor.

8. The optical sensor of claim 1 wherein the means for directing light comprises a second lens being adapted to direct light reflected off the top of the object to the light sensor.

9. The optical sensor of claim 8 wherein the second lens is a wedge lens.

10. The optical sensor of claim 8 wherein the means for directing light reflected further comprises a third lens disposed between the second lens and the light sensor, the third lens being adapted to image the reflected light directed from the second lens onto the light sensor.

11. The optical sensor of claim 1 wherein the light sensor comprises a 1 by 128 pixel line array light detector.

12. The optical sensor of claim 1 wherein the object is generally semi-spherical in shape.

13. The optical sensor of claim 1 further comprising a white surface disposed adjacent to the object, the white surface being significantly more reflective than the object.

14. The optical sensor of claim 1 wherein the object is a drop of blood.

15. The optical sensor of claim 14 in combination with a lance being adapted to puncture skin and to draw a drop of blood and a sensor being adapted to determine the concentration of glucose in the drop of blood.

16. An optical sensor for measuring the volume of an object comprising:
   a source of light adapted to illuminate a side and a top of the object;
   a light sensor adapted to measure an amount of light reflected off the side and off the top of the object;
   a mirror being adapted to direct light reflected off of the side of the object to the light sensor;
   a first lens disposed between the mirror and the light detector, the first lens being adapted to image the reflected light directed from the mirror onto the light sensor;
   a second lens being adapted to direct light reflected off the top of the object to the light sensor; and
   a third lens disposed between the second lens and the light sensor, the third lens being adapted to image the reflected light directed from the second lens onto the light sensor.

17. The optical sensor of claim 16 wherein the second lens is a wedge lens.

18. An optical sensor for measuring the volume of an object comprising:
   a source of light adapted to illuminate a side and a top of the object;
   a light sensor adapted to measure an amount of light reflected off the side and off the top of the object;
   at least one optical device being adapted to direct light reflected off the side of the object to the light sensor, wherein the amount of light reflected off the side of the object correlates to a height of the object;
   at least one optical device being adapted to direct light reflected off the top of the object to the light sensor, wherein the amount of light reflected off the top of the object correlates to a diameter of the object; and
   a processor communicatively coupled to the light sensor, the processor determining the volume of the object from a single height measurement of the object and a single diameter dimension measurement of the object.

19. The optical sensor of claim 18 wherein the light has a wavelength greater than about 750 nanometers.

20. The optical sensor of claim 19 wherein the wavelength is about 800 nanometers.

21. The optical sensor of claim 18 wherein the source of light source comprises an incandescent light.

22. The optical sensor of claim 18 wherein the source of light source comprises a plurality of light emitting diodes.

23. The optical sensor of claim 18 wherein the at least one optical device being adapted to direct light reflected off the side of the object to the light sensor comprises a mirror.

24. The optical sensor of claim 18 wherein the at least one optical device being adapted to direct light reflected off the side of the object to the light sensor further comprises:
   a mirror adapted to direct the light reflected off the side of the object; and
   a first lens adapted to image the reflected light directed from the mirror onto the light sensor.

25. The optical sensor of claim 18 wherein the at least one optical device being adapted to direct light reflected off the top of the object to the light sensor comprises a second lens.

26. The optical sensor of claim 25 wherein the second lens is a wedge lens.

27. The optical sensor of claim 18 wherein the at least one optical device being adapted to direct light reflected off the top of the object to the light detector further comprises:
   a second lens adapted to direct the light reflected off the top of the object; and
   a third lens adapted to image the light directed from the second lens onto the light sensor.

28. The optical sensor of claim 27 wherein the second lens is a wedge lens.

29. The optical sensor of claim 18 wherein the light sensor comprises a 1 by 128 pixel line array light detector.

30. The optical sensor of claim 18 further comprising a white surface disposed adjacent to the object, the white surface being significantly more reflective than the object.

31. An optical sensor for measuring the volume of an object, the object having a side and a top, the optical sensor comprising:
   a source of light being adapted to illuminate the side and the top of the object,
   a light sensor being adapted to measure an amount of light reflected off the side and off the top of the object;
   a first optical device being adapted to reflect a portion of the light from the source of light;
   a second optical device being adapted to direct light reflected from the first optical device onto the side of the object, the first optical device being adapted to direct light reflected off the side of the object to the light sensor, wherein the light reflected off the side of the object and directed to the light sensor correlates to the height of the object; and
   a third optical device being adapted to direct light reflected from the first optical device onto the top of the object, the third optical device also being adapted to direct light reflected off the top of the object to the light sensor, wherein the amount of light reflected off the top of the object and directed to the light sensor correlates to a diameter of the object.

32. The optical sensor of claim 31 wherein the first optical device is a beam splitter.

33. The optical sensor of claim 32 wherein the beam splitter is adapted to reflect about half of the light from the source of light and to transmit about half of the light from the source of light.

34. The optical sensor of claim 31 wherein the second optical device is a mirror.

35. The optical sensor of claim 31 wherein the third optical device is a wedge lens.

36. The optical sensor of claim 31 further comprising a first lens disposed between the second optical device and the light detector, the first lens being adapted to image the light directed from the second optical device onto the light sensor.

37. The optical sensor of claim 31 further comprising a second lens disposed between the third optical device and the light detector, the lens being adapted to image the light directed from the second optical device onto the light sensor.

38. The optical sensor of claim 31 wherein the light sensor comprises a 1 by 128 pixel line array light detector.

39. The optical sensor of claim 31 wherein the object is generally semi-spherical in shape.

40. The optical sensor of claim 31 wherein the object is a drop of a liquid.

41. The optical sensor of claim 40 wherein the liquid is blood.

42. The optical sensor of claim 41 in combination with a lance being adapted to puncture skin and to draw a drop of blood and a sensor being adapted to determine the concentration of glucose in the drop of blood.

43. The optical sensor of claim 31 wherein the light has a wavelength greater than about 750 nanometers.

44. The optical sensor of claim 43 wherein the wavelength is about 800 nanometers.

45. A method of determining the volume of an object, the object having a top and a side, the method comprising:
    illuminating the side and the top of the object with a light from a light source;
    directing light reflected off the side and off the top of the object to a light sensor;
    measuring the amount of light reflected off the side and off the top of the object with the light sensor, wherein the amount of light reflected off the side of the object correlates to a height of the object and the amount of light reflected off the top of the object correlates to a diameter of the object; and
    calculating the volume of the object from a single height measurement of the object and a single diameter dimension measurement of the object.

46. The method of claim 45 wherein the object is generally semi-spherical in shape.

47. The method of claim 46 wherein the calculating the volume of the object comprises dividing by two the product of the square of the height and the diameter.

48. The method of claim 45, wherein directing the light through the first lens to a mirror further comprises expanding the light with the first lens.

49. The method of claim 45 wherein directing the light through the second lens to a wedge lends further comprises expanding the light with the second lens.

50. The method of claim 45 wherein directing the light reflected off the side of the object further comprises:
    directing the light reflected off the side of the object to a first lens with a mirror, and
    imaging the light reflected off the side of the object onto the light sensor with the first lens.

51. The method of claim 50 wherein imaging the light reflected off the side of the object onto the light sensor further comprises transmitting the light through the beam splitter.

52. The method of claim 45 wherein directing the light reflected off the top of the object further comprises:
    directing the light reflected off the top of the object to a second lens with a wedge lens; and
    imaging the light reflected off the top of the object onto the light sensor with the second lens.

53. The method of claim 52 wherein imaging the light reflected off the top of the object onto the light sensor further comprises transmitting the light through the beam splitter.

54. The method of claim 45 wherein the light source has a wavelength greater than about 750 nanometers.

55. The method of claim 54 wherein the wavelength is about 800 nanometers.

56. The method of claim 54 wherein the light source comprises an incandescent light.

57. The method of claim 45 wherein the light source comprises a plurality of light emitting diodes.

58. The method of claim 45 wherein the light detector comprises a 1 by 128 pixel line array light detector.

59. The method of claim 45 wherein the object is a drop of blood, the method further comprising:
    drawing the drop of blood with a lance; and
    determining the glucose concentration level in the blood drop.

60. A method of determining the volume of an object, the object having a top and a side, the method comprising:
    simultaneously reflecting the light source off a beam splitter to a first lens and a second lens;
    directing the light through the first lens to a mirror;
    directing the light onto the side of the object with the mirror;
    directing the light through the second lens to a wedge lens;
    directing the light onto the top of the object;
    directing light reflected off the side and off the top of the object to a light sensor; and
    measuring the amount of light reflected off the side and off the top of the object with the light sensor, wherein the amount of light reflected off the side of the object correlates to a height of the object and the amount of light reflected off the top of the object correlates to a diameter of the object.

61. The method of claim 60 wherein the beam splitter is adapted to reflect about half of the light from the source of light and to transmit about half of the light from the source of light.

* * * * *